United States Patent
Crews et al.

(10) Patent No.: US 11,559,341 B2
(45) Date of Patent: Jan. 24, 2023

(54) SURGICAL INSTRUMENTATION FOR CERVICAL-OCCIPITO FIXATION

(71) Applicant: Aesculap Implant Systems, LLC, Center Valley, PA (US)

(72) Inventors: Robert M Crews, Bartlett, TN (US); Ernie Corrao, Bethel, CT (US); Scott Larsen, Newtown, CT (US)

(73) Assignee: Aesculap AG, Tuttlingen (DE)

( * ) Notice: Subject to any disclaimer, the term of this patent is extended or adjusted under 35 U.S.C. 154(b) by 18 days.

(21) Appl. No.: 17/177,301

(22) Filed: Feb. 17, 2021

(65) Prior Publication Data
US 2021/0346069 A1 Nov. 11, 2021

Related U.S. Application Data

(60) Provisional application No. 62/981,183, filed on Feb. 25, 2020.

(51) Int. Cl.
*A61B 17/80* (2006.01)
*A61B 17/70* (2006.01)

(52) U.S. Cl.
CPC ........ *A61B 17/808* (2013.01); *A61B 17/7055* (2013.01); *A61B 17/7059* (2013.01)

(58) Field of Classification Search
CPC .............. A61B 17/808; A61B 17/1728; A61B 17/1735; A61B 17/7059
See application file for complete search history.

(56) References Cited

U.S. PATENT DOCUMENTS

| | | | | |
|---|---|---|---|---|
| 1,985,108 | A * | 12/1934 | Rush | A61B 17/8866 606/86 R |
| 4,187,840 | A * | 2/1980 | Watanabe | A61B 17/8866 606/86 R |
| 6,533,786 | B1 * | 3/2003 | Needham | A61B 17/7059 606/296 |
| 10,743,920 | B2 * | 8/2020 | Dresher | A61B 17/8009 |
| 2005/0131420 | A1 * | 6/2005 | Techiera | A61B 17/7002 606/99 |
| 2008/0045968 | A1 * | 2/2008 | Yu | A61B 17/1757 606/99 |
| 2009/0018547 | A1 * | 1/2009 | Crews | A61B 17/1739 606/96 |
| 2010/0100131 | A1 * | 4/2010 | Wallenstein | A61B 17/809 606/279 |
| 2012/0022533 | A1 * | 1/2012 | Buettler | A61B 17/1725 606/62 |

(Continued)

*Primary Examiner* — Eduardo C Robert
*Assistant Examiner* — Steven J Cotroneo

(57) ABSTRACT

A plate holder instrument includes a base and a clamp. The clamp is displaceable relative to the base in a longitudinal direction and forms a plate receiving recess with the base. The clamp is displaceable between a released position to allow a bone plate to be loaded into and removed from the plate receiving recess, and a clamped position to lock a plate in the plate receiving recess. An actuator is displaceable relative to the base in a first direction to move the clamp to the released position and a second direction to move the clamp to the clamped position. The plate holder instrument can be combined with one or more surgical instruments, bone plates, screws, tools, taps, depth gauges, screw drivers and/or other accessories as a kit.

18 Claims, 9 Drawing Sheets

(56) References Cited

U.S. PATENT DOCUMENTS

| | | | |
|---|---|---|---|
| 2013/0116733 A1* | 5/2013 | Stoll, Jr. | A61B 17/8866 |
| | | | 606/282 |
| 2017/0238972 A1* | 8/2017 | Sandhu | A61B 17/808 |
| 2017/0281157 A1* | 10/2017 | Hartdegen | A61B 17/1775 |
| 2019/0365438 A1* | 12/2019 | Stamp | A61B 17/0642 |
| 2021/0196328 A1* | 7/2021 | Hammann | A61B 17/1728 |
| 2021/0315567 A1* | 10/2021 | Hartdegen | A61B 17/846 |

* cited by examiner

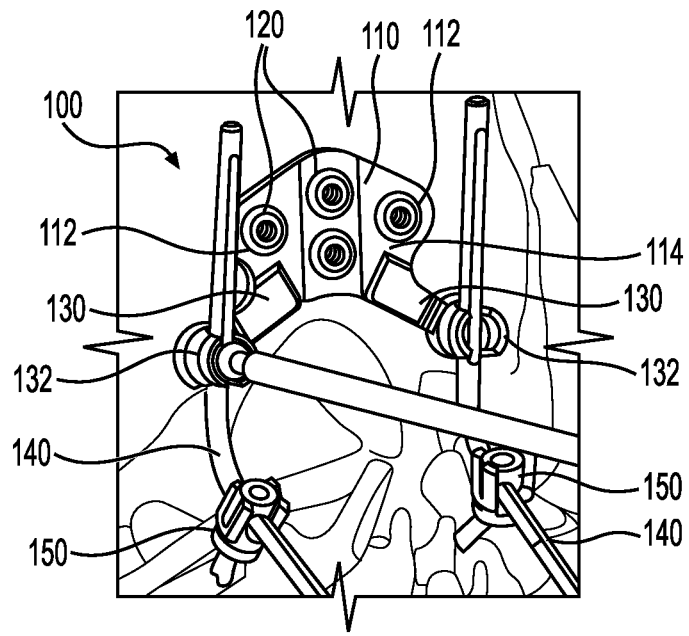
FIG. 1
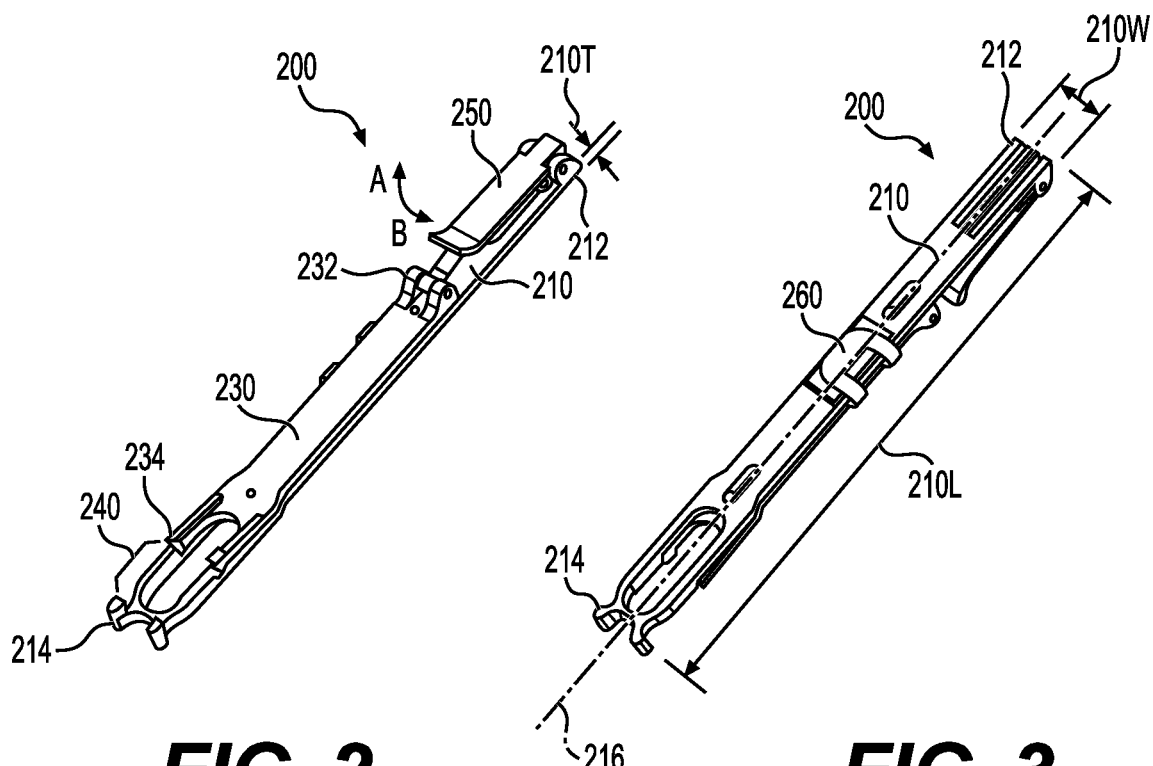
FIG. 2
FIG. 3

SURGICAL INSTRUMENTATION FOR CERVICAL-OCCIPITO FIXATION

FIELD

The present disclosure relates generally to spinal fixation, and more specifically to surgical instruments used for fixation of the cervical spine.

BACKGROUND

Spinal fusion is a procedure in which damaged vertebrae are removed, and vertebral bodies adjacent to the removed vertebrae are fused together with graft material. The spine must be immobilized during fusion. To immobilize the spine, one or more fixation rods are anchored to the vertebrae to limit movement.

Cervical-occipito fixation may be accomplished by using fixation rods attached to a bone plate that, in turn, is anchored to the occiput bone on the posterior of the skull. One example of such a bone plate is described in U.S. Pat. No. 8,348,981 assigned to Aesculap Implant Systems, LLC, the contents of which is incorporated by reference herein in its entirety. Occipital bone plates are attached to the skull with bone screws that are inserted through openings in the bone plates. Prior to inserting the screws, the holes for the screws must be drilled and tapped.

Drilling and tapping holes at the rear of the skull is a difficult procedure that requires a significant amount of force to penetrate the dense cortical bone. The process is further complicated by the angle of approach that is required for instruments. In addition, the drill depth must be controlled with precision, which is difficult to do while at the same time applying significant force on the drill at a difficult angle of approach.

SUMMARY

The aforementioned challenges are addressed in many respects by instruments in accordance with the present disclosure.

In one aspect of the disclosure, a plate holder instrument includes a base having a proximal end and a distal end opposite the proximal end. The base defines a longitudinal axis extending from the proximal end to the distal end in a longitudinal direction. A clamp is displaceable relative to the base in the longitudinal direction and forms a plate receiving recess with the base. The clamp is displaceable between a released position to allow a bone plate to be loaded into and removed from the plate receiving recess, and a clamped position to lock a plate in the plate receiving recess. An actuator is displaceable relative to the base in a first direction to move the clamp to the released position and a second direction to move the clamp to the clamped position.

In another aspect of the disclosure, a plate holder instrument has an actuator with a lever arm pivotally mounted to the proximal end of the base by a hinge.

In another aspect of the disclosure, a plate holder instrument has an actuator with a link member connected between the lever arm and the clamp.

In another aspect of the disclosure, a plate holder instrument has an actuator with a link member having a first link end pivotally coupled to a lever arm and a second link end pivotally connected to a clamp.

In another aspect of the disclosure, a plate holder instrument has a base with a first plate holding surface and a clamp with a second plate holding surface.

In another aspect of the disclosure, a plate holder instrument has a plate receiving recess that extends between a first plate holding surface and a second plate holding surface.

In another aspect of the disclosure, a plate holder instrument has a second plate holding surface that is movable away from a first plate holding surface in response to an actuator being moved relative to a base in a first direction.

In another aspect of the disclosure, a plate holder instrument has a second plate holding surface that is movable toward a first plate holding surface in response to an actuator being moved relative to a base in a second direction.

In another aspect of the disclosure, a plate holder instrument has a first plate holding surface with a first pair of detents projecting from a base, and a second plate holding surface with a second pair of detents projecting from a clamp.

In another aspect of the disclosure, a plate holder instrument has a plate receiving recess with a first ramped surface on a first side of a longitudinal axis and a second ramped surface on a second side of the longitudinal axis, the second ramped surface being non parallel to the first ramped surface.

In another aspect of the disclosure, a plate holder instrument has a base with at least one stop surface and a clamp that has at least one stop member configured to abut the at least one stop surface when the clamp is moved to a clamped position.

In another aspect of the disclosure, a plate holder instrument has a base and clamp that collectively define an aperture adjacent a plate receiving recess, the aperture configured to extend behind a plate secured in the plate receiving recess.

In another aspect of the disclosure, a plate holder instrument has a fastener to detachably couple a guide accessory to the plate holder instrument.

In another aspect of the disclosure, a plate holder instrument has a fastener in the form of a clip.

In another aspect of the disclosure, plate holder instrument has a clamp that is displaceable relative to a base to a cleaning position in which the clamp is separated from the base to facilitate sterilization.

In another aspect of the disclosure, plate holder instrument has an actuator is movable in the first direction to move the clamp from the released position to the cleaning position.

In another aspect of the disclosure, a kit for attaching a bone plate to a posterior area of a patient's skull includes a plate holder instrument. The plate holder instrument includes a base having a proximal end and a distal end opposite the proximal end. The base defines a longitudinal axis extending from the proximal end to the distal end in a longitudinal direction. A clamp is displaceable relative to the base in the longitudinal direction and forms a plate receiving recess with the base. The clamp is displaceable between a released position to allow a bone plate to be loaded into and removed from the plate receiving recess, and a clamped position to lock a plate in the plate receiving recess. An actuator is displaceable relative to the base in a first direction to move the clamp to the released position and a second direction to move the clamp to the clamped position. At least one guide accessory is configured to be detachably coupled to the plate holder instrument.

In another aspect of the disclosure, a kit has at least one guide accessory in the form of at least one drill guide.

In another aspect of the disclosure, a kit has at least one guide accessory in the form of at least one tap guide.

In another aspect of the disclosure, a kit has at least one bone plate.

BRIEF DESCRIPTION OF THE DRAWING FIGURES

The foregoing summary and the following detailed description will be better understood in conjunction with non-limiting examples shown in the drawing figures, of which:

FIG. 1 is a schematic perspective view of a cervical-occipito fixation system featuring a bone plate attached to the posterior of a patient's skull;

FIG. 2 is a front perspective view of a plate holder instrument according the present disclosure;

FIG. 3 is a rear perspective view of the plate holder instrument of FIG. 2;

DETAILED DESCRIPTION

Figure 4:
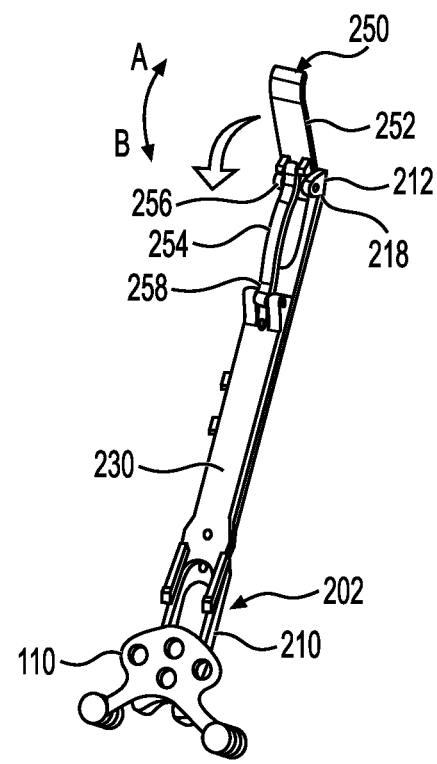
FIG. 4 is another front perspective view of the plate holder instrument of FIG. 2 with a bone plate loaded into the plate holder instrument.

The following section describes different instruments used for fixation of the cervical spine according to the present disclosure.

FIG. 1 shows a cervical-occipito fixation system 100 featuring a bone plate 110 attached to the occipital bone of a patient's skull. The bone plate 110 is anchored to the occipital bone with four bone screws 120. The bone screws 120 are driven through holes 112 in a main body portion 114 of the bone plate. A pair of legs 130 extend outwardly from main body portion 114. Each leg 130 has a socket 132 configured to support a cervical fixation rod 140. Cervical fixation rods 140 are connected to bone anchor assemblies 150 implanted in the spine.

FIGS. 2 and 3 show a plate holder instrument 200. Plate holder instrument 200 is configured to hold a bone plate in a desired position where it is to be attached to an occipital bone. Plate holder instrument 200 also works with other accessories, as will be described, to drill and tap screw holes in the occipital bone. Moreover, plate holder instrument 200 can be used to hold the bone plate in position as bone screws are driven through the tapped screw holes to anchor the bone plate to the occipital bone.

Plate holder instruments according to the present disclosure have components that move relative to one another to engage and disengage a bone plate. The components can have various structures. Relatively long and thin components with small thicknesses allow the plate holder instrument to have a long and thin profile so that the instrument can access the occipital bone while taking up minimal space. In the present example, plate holder 200 has a plate-shaped base 210 with an axial length 210L, width 210W, and thickness 210T. Thickness 210T is a small fraction of width 210W, and width 210W is a small fraction of axial length 210L. Base 210 has a proximal end 212 and a distal end 214 opposite the proximal end. Base 210 also defines a longitudinal axis 216 extending from the proximal end to the distal end in a longitudinal direction.

Plate holder 200 includes a plate-shaped clamp 230. Clamp 230 has a proximal end 232 and distal end 234 opposite the proximal end. In addition, clamp 230 is connected to base 210 in an axially displaceable arrangement. In this arrangement, clamp 230 is displaceable relative to base 210 in the longitudinal direction. Clamp 230 forms a plate receiving recess 240 with base 210. Plate receiving recess 240 is sized to receive and support a base plate. Clamp 230 is displaceable relative to base 210 between a released position and a clamped position. In the released position, clamp 230 allows a bone plate, like bone plate 110, to be loaded into and removed from plate receiving recess 240. In the clamped position, clamp 230 securely engages a bone plate in the plate receiving recess 240, so that the bone plate is locked in the plate receiving recess.

Plate holder 200 further includes an actuator 250. Actuator 250 is displaceable relative to base 210 in a first direction A to move clamp 230 to the released position. Actuator 250 is also displaceable relative to base 210 in a second direction B to move clamp 230 to the clamped position.

Figure 5:
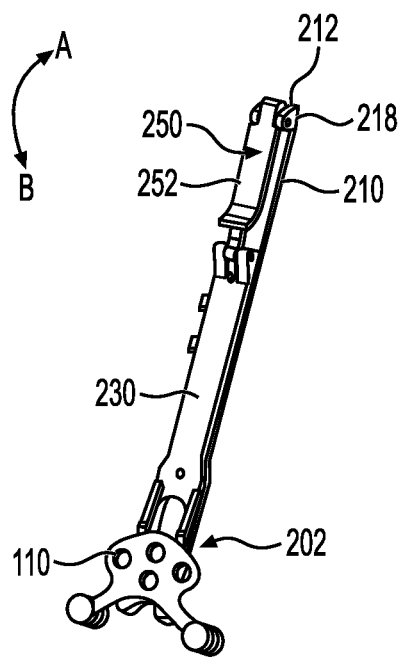
FIG. 5 is another front perspective view of the plate holder instrument of FIG. 2 with the bone plate clamped in the plate holder instrument.

FIGS. 4 and 5 show plate holder 200 with bone plate 110 loaded into plate receiving recess 240. When actuator 250 is moved in first direction A as shown in FIG. 4, clamp 230 is moved to the released position. In this position, plate receiving recess 240 is expanded, providing clearance to allow the loading of bone plate 110 into the plate receiving recess between base 210 and clamp 230. When actuator 250 is moved in the second direction B as shown in FIG. 5, clamp 230 is moved to the clamped position. In this position, plate receiving recess 240 is contracted or reduced in size to enclose bone plate 110 on two sides. In this arrangement, base 210 and clamp 230 collectively form a vise 202 that can be opened and closed via actuator 250 to unclamp or clamp a bone plate.

Figure 19:
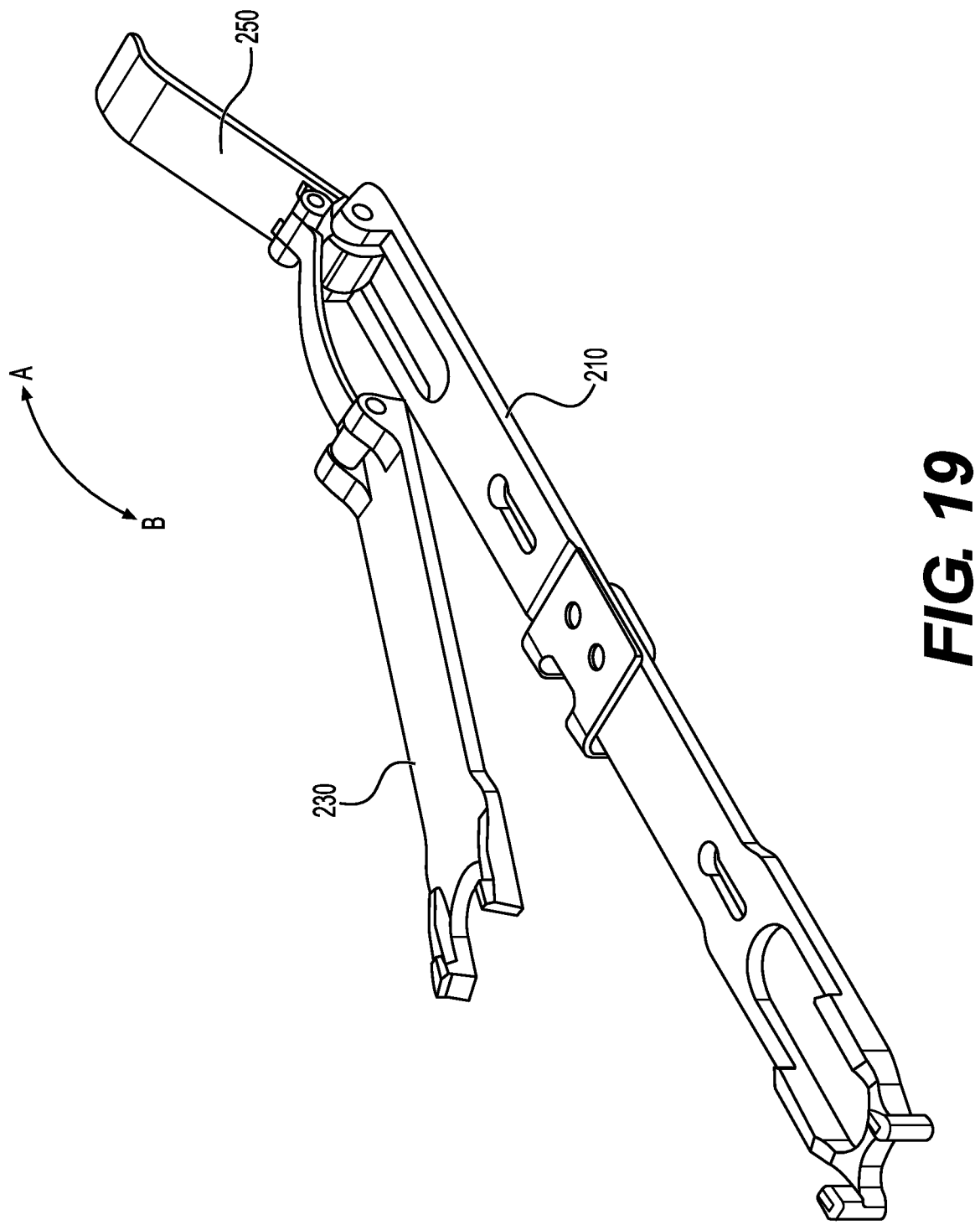
FIG. 19 is another front perspective view of the plate holder instrument of FIG. 2, in which the plate is removed and the actuator is moved to a cleaning position to permit components to be sterilized.

Actuator 250 can be moved in first direction A beyond the released position to a cleaning position, as shown in FIG. 19. In this position, clamp 230 is detached from base 210, which allows the components to be sterilized.

Referring back to FIGS. 4 and 5, actuator 250 includes a lever arm 252 pivotally mounted to proximal end 212 of base 210 by a hinge 218. Actuator 250 further includes a link member 254 connected between lever arm 252 and clamp 230. Link member 254 has a first link end 256 pivotally coupled to lever arm 252 and a second link end 258 pivotally connected to clamp 230.

Figure 6:
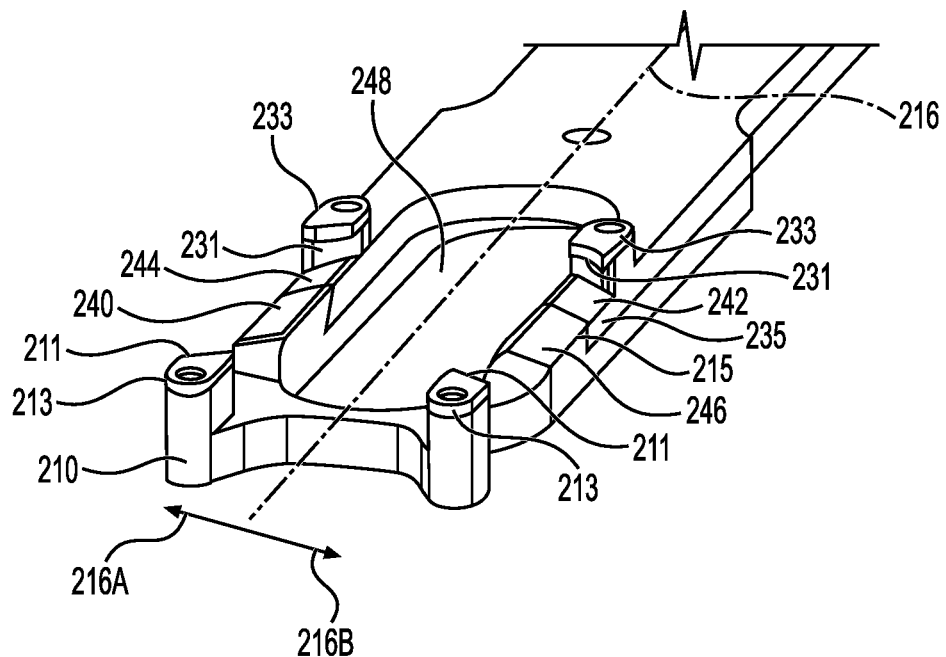
FIG. 6 is an enlarged truncated perspective view the plate holder instrument of FIG. 2, showing details at one end.

Referring to FIG. 6, base 210 includes a first plate holding surface 211 and clamp 230 includes a second plate holding surface 231. Plate receiving recess 240 extends between first plate holding surface 211 and second plate holding surface 231. Second plate holding surface 231 is movable away from first plate holding surface 211 in response to actuator 250 being moved relative to base 210 in first direction A. Second plate holding surface 231 is movable toward first plate holding surface 211 in response to actuator 250 being moved relative to base 210 in second direction B.

The occipital bone typically has a curvature. Bone plates with a flat profile are difficult to secure to a curved bone surface. Therefore, it is often desirable for the bone plate to be bent or otherwise shaped so as to have a curved contour or face that conforms to the natural curvature of the occipital bone. For example, the plate can be bent so that the side of the plate to be secured against the occipital bone has a concave shape.

Figure 7:
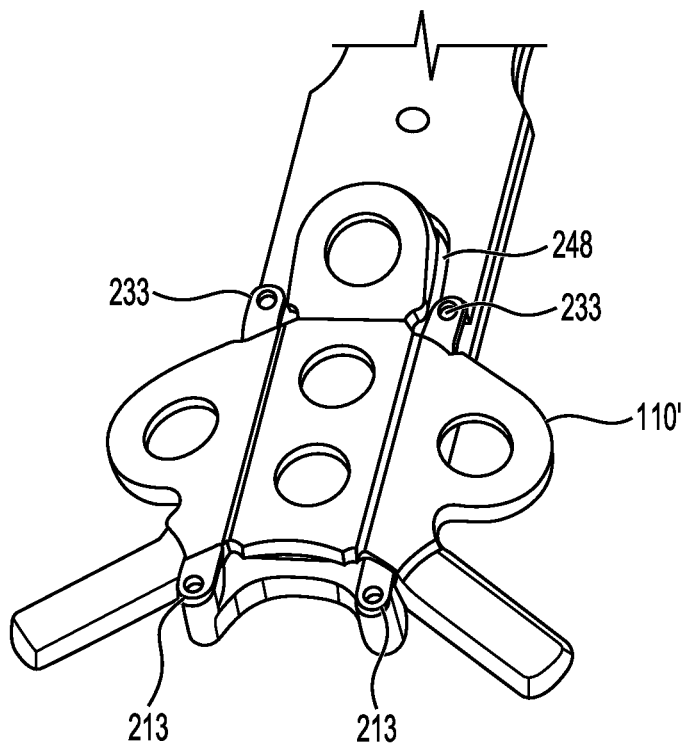
FIG. 7 is another enlarged truncated perspective view of the plate holder instrument of FIG. 2, with a bone plate secured in one end.

Plate holders and recesses according to the present disclosure can have one or more surfaces that conform to the curvature of curved bone plates. Referring to FIG. 7, plate receiving recess 240 has a contoured support surface 242 that conforms to the curved rear face of a bone plate 110'. In particular, plate receiving recess 240 includes a first ramped surface 244 on a first side 216A of longitudinal axis 216. Plate receiving recess 240 also includes a second ramped surface 246 on a second side 216B of longitudinal axis 216. Second ramped surface 246 is non parallel to first ramped surface 244. Moreover, first ramped surface 244 and second ramped surface 246 are inclined toward one another as they extend toward longitudinal axis 216. In this arrangement, first and second ramped surfaces 244, 246 collectively form a V-shaped or U-shaped support surface 246 that conforms to the curvature of bone plate 110'.

First plate holding surface 211 includes a first pair of detents 213 projecting from base 210. Similarly, second plate holding surface 231 includes a second pair of detents 233 projecting from clamp 230. First pair of detents 213 and second pair of detents 233 only contact bone plate 110' at four locations along the perimeter of the bone plate.

Plate holders according to the present disclosure can include stop mechanisms for limiting displacement of the clamp relative to the plate as the plate is moved to the clamped position. Stop mechanisms can be used to prevent a bone plate from being clamped too tightly, potentially deforming and damaging the bone plate. In the present example, base 210 includes a pair of stop surfaces 215 that face toward proximal end 212 of the base. In addition, clamp 230 includes a pair of stop members 235 that define distal end 234 of the clamp. Stop members 235 are configured to abut stop surfaces 215 when clamp 230 is moved to the clamped position, preventing second plate holding surface 231 from moving any closer to first plate holding surface 211.

Base 210 and clamp 230 collectively define an aperture 248 adjacent plate receiving recess 240. Aperture 248 is configured to extend behind the holes of a bone plate secured in plate receiving recess 240, as shown for example in FIG. 7, so that a clear unobstructed path extends through the holes in the plate to occipital bone when the plate holder and plate are held against the occipital bone.

Figure 20:
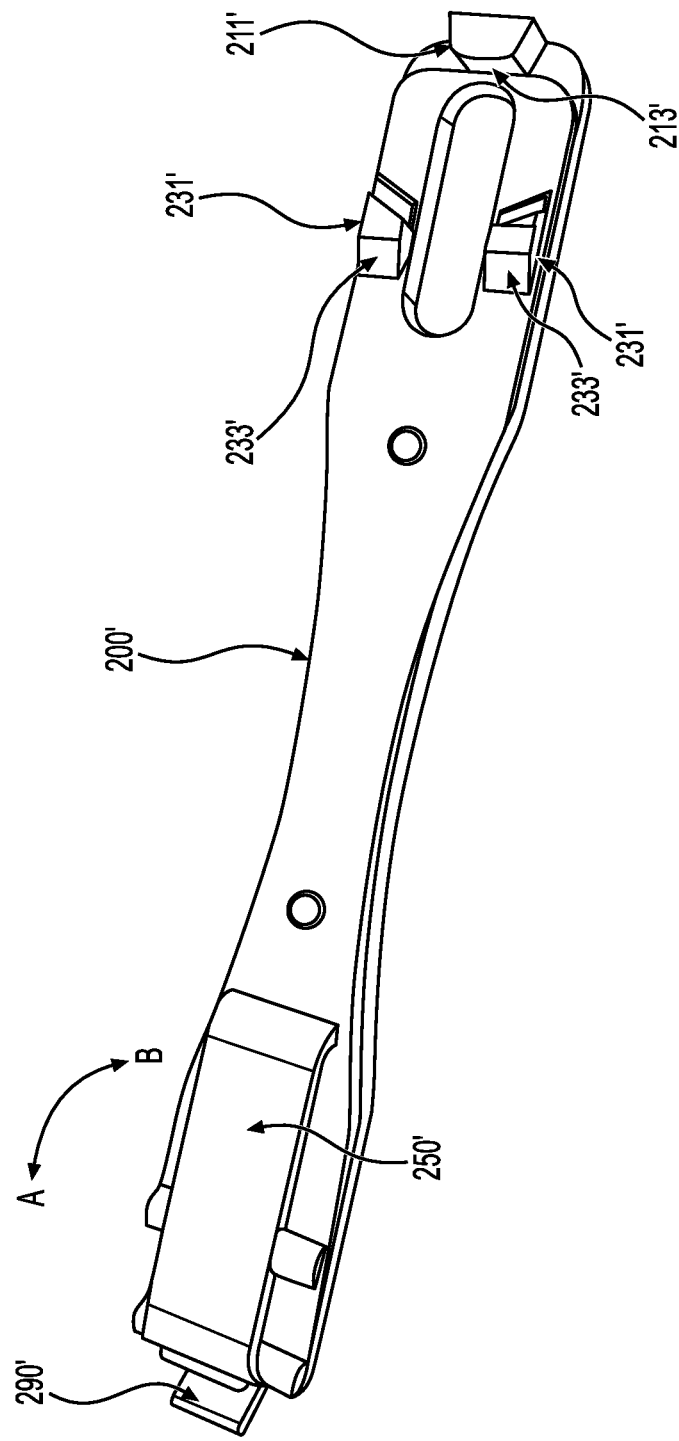
FIG. 20 is a perspective view of another plate holder instrument according to the present disclosure.

Plate holders according to the present disclosure can have various plate holding structures and configurations. For example, a plate holding surface can be comprised of a single detent, rather than a pair of detents. Referring to FIG. 20, a plate holder 200' is shown with a first plate holding surface 211' comprised of a single detent 213', and a second plate holding surface 231' with a pair of detents 233'. In this arrangement, the single detent 213' and pair of detents 233' contact a bone plate at three locations along the perimeter of the bone plate. Plate holder 200' also includes a guard 290' that limits how far actuator 250' can be pivoted in the first direction A.

Figure 10:
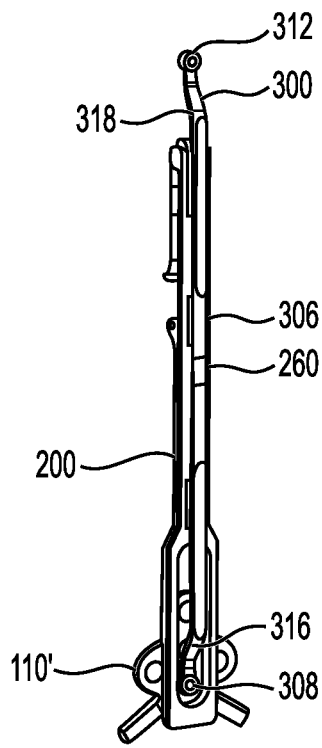
FIG. 10 is a front perspective view of a third combination drill guide and tap guide attached to the plate holder instrument of FIG. 2 and bone plate according the present disclosure.

Plate holders according to the present disclosure are configured to work with different accessories, including guides that aid in the drilling and tapping of screw holes in the occipital bone, and guides for driving screws through a bone plate. In the present example, plate holder 200 includes a fastener in the form of a clip 260, the rear facing portion of which is shown in FIGS. 3 and 10. Clip 260 is configured to detachably couple a guide accessory to the plate holder.

Plate holders according to the present disclosure can be marketed as stand-alone instruments. Alternatively, plate holders according to the present disclosure can be marketed with one or more accessories. Moreover, plate holders according to the present disclosure can be marketed as part of a surgical set that includes various surgical instruments, bone plates, screws, tools, taps, depth gauges, screw drivers and other accessories.

For example, kits according to the present disclosure can include accessories for drilling pilot holes in the occipital bone. Such accessories can include surgical drills, drill bits, and drill guides. Kits according to the present disclosure can also include accessories for tapping screw holes in the occipital bone. Tapping screw holes can involve driving a tapping instrument into a pilot hole to form threading in the screw hole. Thus, kits according to the present disclosure can include taps and tapping guides.

Kits according to the present disclosure can also include one or more bone plates. For example, a kit can include a set of bone plates, with the bone plates differing in terms of their dimensions, curvatures, hole diameters, hole arrangements and/or other design parameters.

Figure 8:
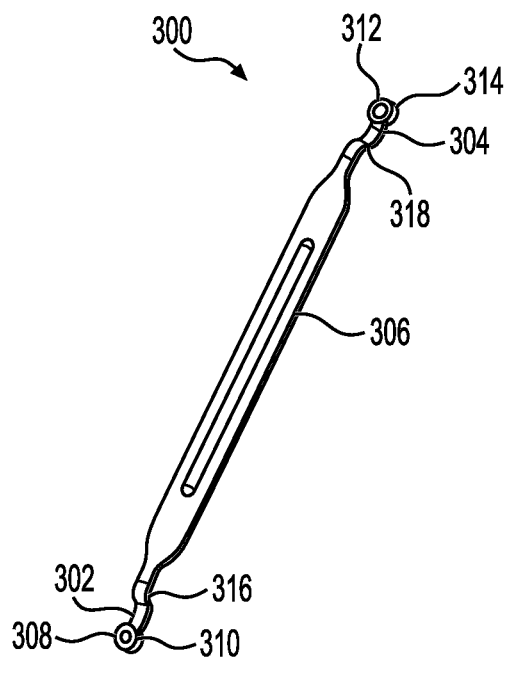
FIG. 8 is a front perspective view of a first combination drill guide and tap guide according the present disclosure.

Guide accessories according to the present disclosure can include combination guides featuring a first end for guiding the drilling of a pilot hole, and a second end for guiding the tapping of screw hole. FIG. 8 shows one example of a combination guide 300 used for tapping a screw hole to receive a 4.5 mm screw in a mini-access procedure. Combination guide 300 has a first end 302, a second end 304 and an elongated body 306 extending between the first end and second end. First end 302 has a cylindrical guide ring 308 adapted to receive a drill bit, so as to serve as a drill guide 310. Second end 304 has a cylindrical guide ring 312 adapted to receive a tapping tool, so as to serve as a tapping guide 314. First end 302 is connected to elongated body 306 by a first dog leg section 316, and second end 304 is connected to the elongated body by a second dog leg section 318.

Figure 9:
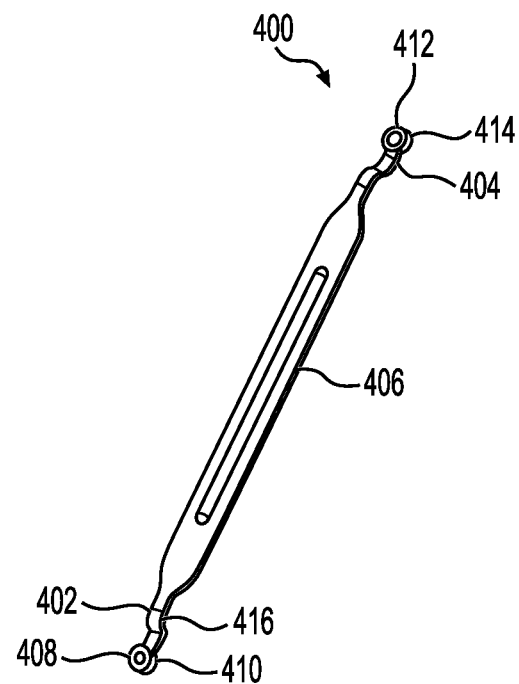
FIG. 9 is a front perspective view of a second combination drill guide and tap guide according the present disclosure.

FIG. 9 shows an example of another combination guide 400 used for tapping a screw to receive a 5.5 mm screw hole in a mini-access procedure. Combination guide 400 has a first end 402, a second end 404 and an elongated body 406 extending between the first end and second end. First end 402 has a cylindrical guide ring 408 adapted to receive a drill bit, so as to serve as a drill guide 410. Second end 404 has a cylindrical guide ring 412 adapted to receive a tapping tool, so as to serve as a tapping guide 414. First end 402 is connected to elongated body 406 by a first dog leg section 416, and second end 404 is connected to the elongated body by a second dog leg section 418.

Figure 11:
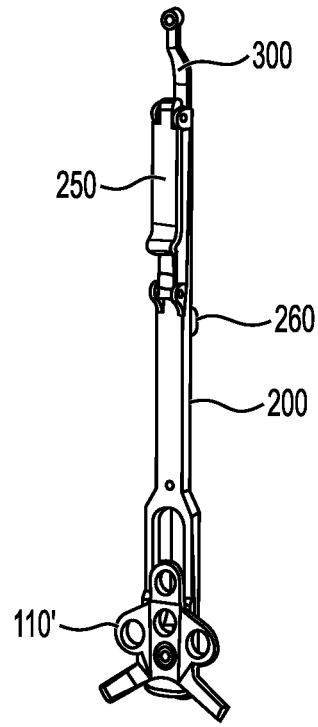
FIG. 11 is a rear perspective view of the third combination drill guide and tap guide attached to the plate holder instrument and plate of FIG. 10.

The elongated bodies 306, 406 of combination guides 300, 400 are configured to be inserted into clip 260 of plate holder 200 and releasably retained by the clip. Referring to FIGS. 10 and 11, plate holder 200 is shown with combination guide 300 inserted in clip 260 and aligned with a bone plate 110' loaded in the plate holder. It will be appreciated that combination guide 400 can be inserted in clip 260 and used with plate holder 200 and plate 110' in the same manner. Therefore, only the structural and functional aspects of combination guide 300 will be described, with the understanding that the structural and functional aspects of combination guide 400 are identical in all respects, with the only difference being the size of the guide rings.

First and second dog leg sections 316, 318 create offsets that allow guide rings 308, 312 to be positioned flush against bone plate 110', while elongated body 306 is positioned outwardly from the bone plate. These offsets are necessary to allow the guide rings 308, 312 to be positioned as close to bone plate 110' as possible, while allowing elongated body 306 to be coupled over top of plate holder 200 in a straddling arrangement.

Figure 12:
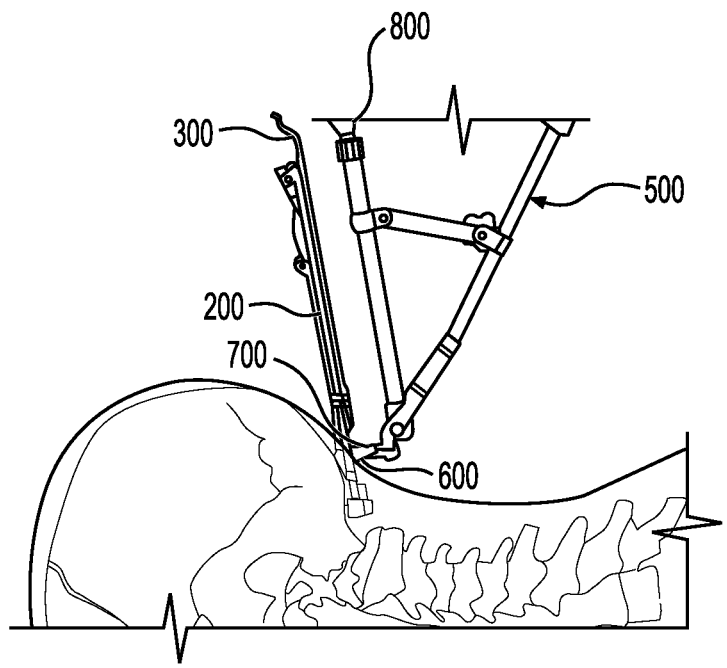
FIG. 12 is a schematic side view of the third combination drill guide and tap guide attached to the plate holder instrument and plate of FIG. 10, shown during drilling of a screw hole.
Figure 13:
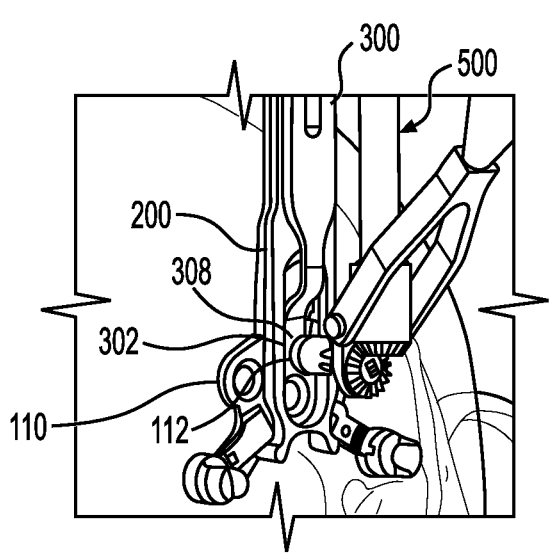
FIG. 13 is an enlarged perspective view showing details of the third combination drill guide and tap guide, plate holder instrument, and plate during drilling of a screw hole.

Plate holders according to the present disclosure can also be used with angled instruments for guiding surgical drills and tapping instruments. FIGS. 12 and 13 show plate holder 200 holding bone plate 110 against the occipital bone during the drilling of a pilot hole. An angled gear instrument 500 with drill bit 600 and depth stop 700 drill the pilot hole, with torque provided by a drill driver 800. In this instance, combination guide 300 is coupled to plate holder 200 with guide ring 308 on first end 302 aligned with a hole 112 in bone plate 110.

Figure 14:
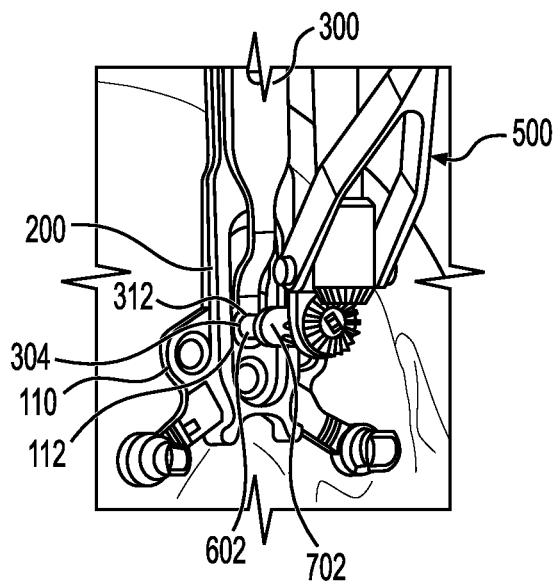
FIG. 14 is an enlarged perspective view showing details of the third combination drill guide and tap guide, plate holder instrument, and plate during tapping of a screw hole.

FIG. 14 shows plate holder 200 holding bone plate 110 against the occipital bone during tapping of the screw hole. Angled gear instrument 500 has a tap 602 and depth stop 702. In this instance, combination guide 300 is coupled to plate holder 200 with guide ring 312 on second end 304 aligned with a hole 112 in bone plate 110.

Figure 15:
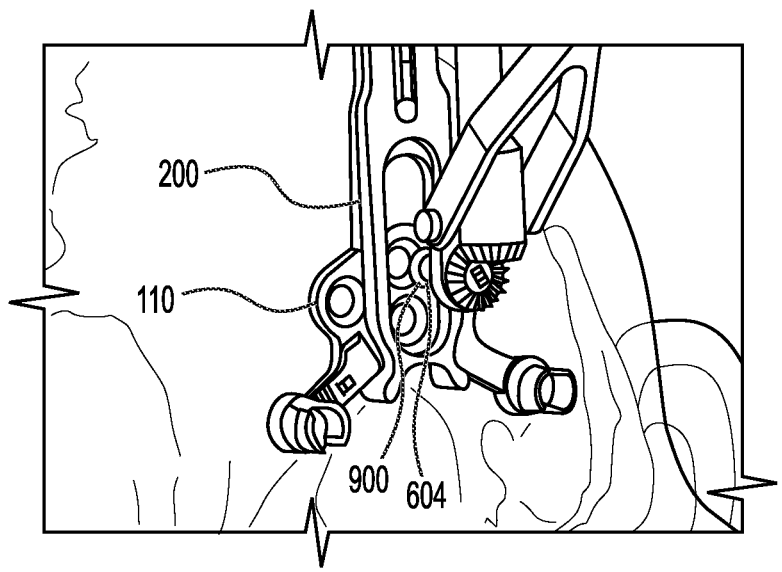
FIG. 15 is an enlarged perspective view showing details of the plate holder instrument and plate during insertion of a screw through the plate and into a tapped screw hole.

FIG. 15 shows plate holder 200 holding bone plate 110 against the occipital bone as the bone plate is anchored to the occipital bone. In this instance, the tapped screw hole is prepared, and combination guide 300 is therefore removed from plate holder 200. A first plate screw 900 is placed on a driver bit 604 attached to angled gear instrument 500. Torque applied to angled gear instrument 500 drives first plate screw 900 through a first hole in bone plate 110 and into a tapped hole to anchor the bone plate to the occipital bone. Once first plate screw 900 is driven into the screw hole, angled gear instrument 500 can be detached, loaded with a second plate screw, and maneuvered to a second hole in bone plate 110 to drive the second plate screw through the second hole and into the occipital bone. This process can be repeated for any other screw holes that are tapped behind bone plate 110.

Figure 16:
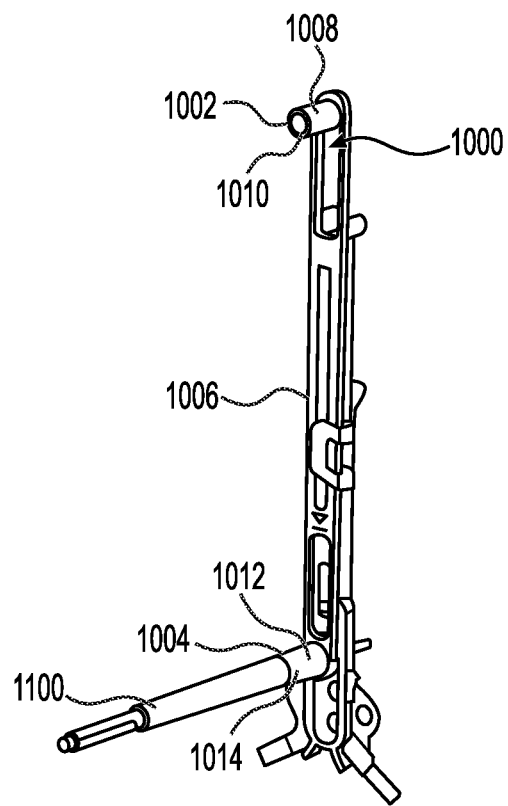
FIG. 16 is a perspective view of another plate holder instrument and plate attached to a fourth combination drill guide and tap guide according to the present disclosure.
Figure 17:
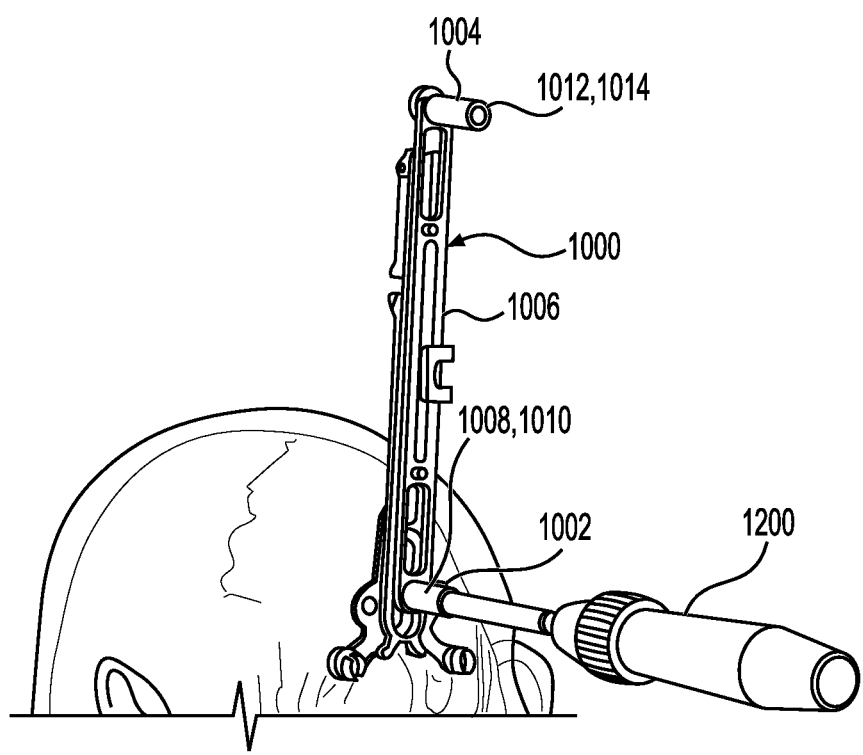
FIG. 17 is a schematic perspective view of the plate holder instrument, plate and fourth combination drill guide and tap guide of FIG. 16 with a tapping instrument.

FIGS. 16 and 17 show an alternate combination guide 1000 that can be used in an open procedure. Combination guide 1000 has a first end 1002, a second end 1004 and an elongated body 1006 extending between the first end and second end. First end 1002 has a cylindrical guide ring 1008 adapted to receive either a drill bit or a tap bit. Second end 1004 also has a cylindrical guide ring 1012 adapted to receive either a drill bit or tap bit. FIG. 16 shows a tap bit 1100 in guide ring 1012, and FIG. 17 shows a tap bit 1200 in guide ring 1008. Unlike combination guides 300, 400, combination guide 1000 does not have dog leg sections between the elongated body and guide rings.

Figure 18:
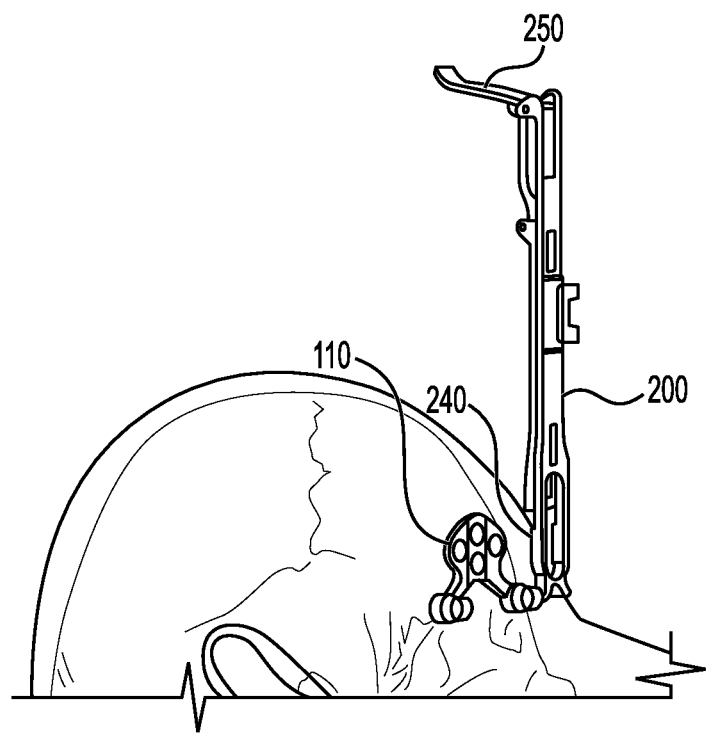
FIG. 18 is a schematic perspective view of a plate holder instrument according to the present disclosure being detached from a bone plate after the bone plate is anchored to a patient's occipital bone.

FIG. 18 shows bone plate 110 anchored to the occipital bone. Actuator 250 of plate holder 200 is moved to the release position to disengage bone plate 110 from the plate receiving recess 240.

The instruments described herein can be manufactured using various materials, including but not limited to various alloys of stainless steel. Alloy grade can be selected based on desired strength, hardness, corrosion resistance, galling properties and other performance criteria.

Accordingly, it is intended that the appended claims cover all such variations as fall within the scope of the present disclosure.

What is claimed is:

1. A plate holder instrument comprising:
    a base having an upper surface and a lower surface, a proximal end and a distal end opposite the proximal end, the base defining a longitudinal axis extending from the proximal end to the distal end in a longitudinal direction;
    a clamp disposed on the upper surface of the base and having a proximal end and a distal end opposite the proximal end, the clamp being displaceable relative to the base on the upper surface of the base in the longitudinal direction and forming a plate receiving recess on the upper surface of the base between the distal end of the clamp and the distal end of the base, the clamp being displaceable between a released position to allow a bone plate to be loaded into and removed from the plate receiving recess, and a clamped position to lock a plate in the plate receiving recess; and
    an actuator displaceable relative to the base in a first direction to move the clamp to the released position and a second direction to move the clamp to the clamped position.

2. The plate holder instrument of claim 1, wherein the actuator comprises a lever arm pivotally mounted to the proximal end of the base by a hinge.

3. The plate holder instrument of claim 2, wherein the actuator further comprises a link member connected between the lever arm and the clamp.

4. The plate holder instrument of claim 3, wherein the link member has a first link end pivotally coupled to the lever arm and a second link end pivotally connected to the clamp.

5. The plate holder instrument of claim 1, wherein the clamp is movable away from the base in response to the actuator being moved relative to the base in the first direction.

6. The plate holder instrument of claim 1, wherein the clamp is movable toward the base in response to the actuator being moved relative to the base in the second direction.

7. The plate holder instrument of claim 1, wherein the base comprises a first pair of detents projecting from the upper surface of the base, and the clamp comprises a second pair of detents projecting from an upper surface of the clamp.

8. The plate holder instrument of claim 1, wherein the plate receiving recess comprises a first ramped surface on a first side of the longitudinal axis and a second ramped surface on a second side of the longitudinal axis, the second ramped surface being non parallel to the first ramped surface.

9. The plate holder instrument of claim 1, wherein the base comprises at least one stop surface and wherein the clamp comprises at least one stop member configured to abut the stop surface when the clamp is moved to the clamped position.

10. The plate holder instrument of claim 1, wherein the base and the clamp collectively define an aperture adjacent the plate receiving recess, the aperture configured to extend behind a plate secured in the plate receiving recess.

11. The plate holder instrument according to claim 1, further comprising a fastener to detachably couple a guide accessory to the plate holder instrument.

12. The plate holder instrument of claim 11, wherein the fastener comprises a clip.

13. The plate holder instrument of claim 1, wherein the clamp is further displaceable relative to the base to a cleaning position in which the clamp is separated from the base to facilitate sterilization.

14. The plate holder instrument of claim 13, wherein the actuator is movable in the first direction to move the clamp from the released position to the cleaning position.

15. A kit for attaching a bone plate to a posterior area of a patient's skull, the kit comprising:

a plate holder instrument, the plate holder instrument comprising:
  a base having an upper surface and a lower surface, a proximal end and a distal end opposite the proximal end, the base defining a longitudinal axis extending from the proximal end to the distal end in a longitudinal direction;
  a clamp disposed on the upper surface of the base and having a proximal end and a distal end opposite the proximal end, the clamp being displaceable relative to the base on the upper surface of the base in the longitudinal direction and forming a plate receiving recess on the upper surface of the base between the distal end of the clamp and the distal end of the base, the clamp being displaceable between a released position to allow a bone plate to be loaded into and removed from the plate receiving recess, and a clamped position to lock a plate in the plate receiving recess; and
  an actuator displaceable relative to the base in a first direction to move the clamp to the released position and a second direction to move the clamp to the clamped position; and
at least one guide accessory configured to be detachably coupled to the plate holder instrument.

16. The kit of claim 15, wherein the at least one guide accessory comprises at least one drill guide.

17. The kit of claim 15, wherein the at least one guide accessory comprises at least one tap guide.

18. The kit according to any of claims 15-17, further comprising at least one bone plate.

* * * * *